United States Patent [19]

Caunt et al.

[11] 4,051,307
[45] Sept. 27, 1977

[54] POLYMERIZATION PROCESS

[75] Inventors: Anthony David Caunt, Welwyn Garden City; Michael Stanley Fortuin, St. Albans, both of England

[73] Assignee: Imperial Chemical Industries Limited, London, England

[21] Appl. No.: 367,006

[22] Filed: June 4, 1973

[30] Foreign Application Priority Data

| June 9, 1972 | United Kingdom | 27008/72 |
| June 9, 1972 | United Kingdom | 27009/72 |
| July 7, 1972 | United Kingdom | 31884/72 |
| Feb. 9, 1973 | United Kingdom | 7985/73 |
| Feb. 19, 1973 | United Kingdom | 7986/73 |

[51] Int. Cl.² ........................ C08F 4/66; C08F 10/06
[52] U.S. Cl. .................. 526/77; 252/429 B; 526/128; 526/139; 526/351; 526/906
[58] Field of Search ............. 260/94.9 CA, 94.9 CB, 260/94.9 C, 93.7, 94.4, 94.6; 252/429 B, 431 P, 437, 435; 526/139, 77

[56] References Cited

U.S. PATENT DOCUMENTS

| 3,415,801 | 12/1968 | Coover et al. | 260/94.9 CB |
| 3,484,424 | 12/1969 | Moberly | 260/94.9 C |
| 3,502,634 | 3/1970 | Stedefeder et al. | 260/94.9 C |
| 3,534,006 | 10/1970 | Kamaishi et al. | 260/93.7 |
| 3,558,586 | 1/1971 | Fodor | 260/93.7 |
| 3,629,222 | 12/1971 | Coover et al. | 260/93.7 |
| 3,639,375 | 2/1972 | Staiger et al. | 260/94.9 C |
| 3,644,320 | 2/1972 | Sugiura et al | 260/93.7 |
| 3,701,763 | 10/1972 | Wada et al. | 260/94.9 B |
| 3,721,721 | 3/1973 | Maemoto et al. | 252/431 P |
| 3,752,797 | 8/1973 | Gordon et al. | 260/94.9 CB |
| 3,766,160 | 10/1973 | Caunt | 260/94.9 C |

FOREIGN PATENT DOCUMENTS

| 448,516 | 4/1969 | Japan |
| 4,539,621 | 12/1970 | Japan |
| 1,170,589 | 11/1969 | United Kingdom |

*Primary Examiner*—Edward J. Smith
*Attorney, Agent, or Firm*—Cushman, Darby & Cushman

[57] ABSTRACT

An olefine polymerization catalyst includes a complex compound of phosphorus having the general formula

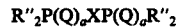

where the various groups are defined. Typical phosphorus compounds include

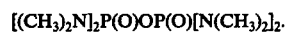

Catalyst systems containing these phosphorus compounds give a high rate of polymerization together with a low proportion of soluble polymer. The phosphorus compound can be ball-milled with the titanium compound to give an improved effect.

20 Claims, No Drawings

POLYMERIZATION PROCESS

The present invention relates to catalysts for the polymerisation of olefines and in particular to materials suitable for use as the third component in such catalysts and catalysts including such third components.

The low pressure polymerisation of olefines, particularly ethylene and propylene, to give high molecular weight polymers has been practiced commercially for several years. The catalyst used for such polymerisations is commonly referred to as a "Ziegler" catalyst and this type of catalyst comprises a compound of a transition metal and an organo-metallic compound of aluminium or an element of Group I or II.

In order to obtain polymers having a high proportion of crystallinity the catalysts used normally comprise a solid compound of a transition metal wherein the transition metal has a valency below its maximum, together with the organo-metallic compound. The transition metal compound is usually a halide and for the production of crystalline polymers the most widely used compound is titanium trichloride, which term is used to include pure titanium trichloride and also impure titanium trichloride associated or combined with other compounds, typically aluminum chloride, and produced by the reduction of titanium tetrachloride with, for example, aluminium metal or organo-aluminium compounds. The most extensively used organo-metallic compound is an organo-aluminium compound such as an aluminium trialkyl or an aluminium dialkyl halide.

Propylene can be polymerised with titanium trichloride and an organo-aluminium compound to give a high yield of polymer based on the catalyst used. However, the polymer produced still contains appreciable quantities of catalyst residues and for most applications it is necessary to remove most of these catalyst residues, this being done by washing with a suitable reagent to remove the catalyst. Typically, the polymer is first treated with an alcohol to terminate catalytic activity and then washed several times with water to remove the catalyst. Such catalyst removal operations increase the cost of producing the polymer.

Attempts have been made to eliminate the need to remove catalyst residues by polymerising the monomer to give a yield of polymer based on catalyst used which is considerably in excess of the yield normally obtained. When polymerising to such high yields the amount of catalyst remaining in the polymer is relatively small, for example, less than 50 parts per million by weight based on the polymer obtained. A disadvantage of polymerising to very high yields is that the polymer obtained has a tendency to contain a higher proportion of soluble polymer than is contained in polymer produced in the more normal yields.

Attempts have been made to reduce the proportion of soluble polymer produced by including a third component in the catalyst system. Whilst some of these third components do reduce the amount of soluble polymer produced, in many cases the polymerisation rate is adversely affected by the third component.

According to the present invention there is provided an olefine polymerisation catalyst comprising (1) a solid compound of a transition metal wherein the said metal has a valency below its maximum, (2) an organo-metallic compound of aluminium or of a non-transition metal of Group II of the Periodic System, or a complex of an organo-metallic compound of a non-transition metal of Group I or II of the Periodic System and an organo-aluminium compound; and (3) at least one phosphorus compound selected from materials of the formulae (a) $R_{3-n}P(Q)(E-Z-G)_n$

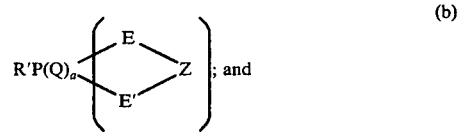
(b)

(c) $R''_2P(Q)_aXP(Q)_aR''_2$ wherein
each R is independently halogen, a hydrocarbyl group, a group $-NR'''_2$ or $-OR'''$, or a heterocyclic group;
R' is R or a group (E—Z—G);
R" is R' or both the R" groups attached to the same P atom together to form a group

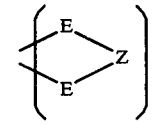

R''' is a hydrocarbyl group;
X is $-O-$, $-NR''''-$, $-E(CH_2)_mE-$ or

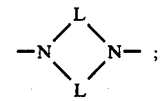

R'''' is a hydrogen or R''',
L is a bivalent hydrocarbyl radical and each L may be the same or different;
each E is $-O-$, $-S-$ or $-NR'''-$ and may be the same or different;
E' is $-S-$ or $-NR'''-$;
G is $-OR'''$, $-SR'''$, $-NR'''_2$, $-PR'''_2$ or a heterocyclic ring system whereof the heteroatom is O, S, N or P;
Q is an oxygen or sulphur atom;
Z is a bivalent hydrocarbyl radical such that E and G or E and E' or E and E are separated by not more than 3 carbon atoms;
each a is independently zero or 1;
m is a positive integer; and
n is 1, 2 or 3.

The transition metal is a metal of the Groups IVA to VIII of the Periodic Table preferably Groups IVA to VIA and can be, for example, titanium, zirconium or vanadium. It is preferred that the transition metal compound is a transition metal halide or oxyhalide (for example $VOCl_2$) and it is particularly preferred to use titanium trichloride especially a solid solution of titanium trichloride with aluminium chloride for example the material obtained by reduction of $TiCl_4$ with aluminium metal as described in British Pat. Specification No. 877 050, as component (1) of the catalyst. Component (2) can include Grignard reagents which are substantially ether free, $Mg(AlEt_4)_2$ or $Mg(C_6H_5)_2$. The aluminium compound can be lithium aluminium tetraalkyl and is preferably an aluminium hydrocarbyl halide, an aluminium hydrocarbyl sulphate, an aluminium hydrocarbyl oxyhydrocarbyl or particularly an aluminium trihydrocarbyl or dihydrocarbyl aluminium halide or hydride such as an aluminium trialkyl or dialkyl aluminium halide or hydride, especially aluminium triethyl or diethyl aluminium chloride since catalysts including aluminium triethyl give a high polymerisation rate whilst catalysts including diethyl aluminium chloride give a relatively low percentage yield of undesirable soluble ("atactic") polymer. As component (2) a mixture of compounds may be used, for example a mixture of an aluminium trialkyl and an aluminium dialkyl halide. Optionally the catalyst can include zinc hydrocarbyl compounds such a zinc diethyl or, in the presense of organo-aluminium compounds, zinc salts such as zinc chloride.

Thus, preferred catalysts in accordance with the present invention comprise (1) titanium trichloride, (2) an aluminium trihydrocarbyl or dihydrocarbyl aluminium halide or hydride, preferably aluminium triethyl or aluminium diethyl chloride and (3) at least one phosphorus compound selected from materials of the formulae (a) $R_{3-n}P(Q)(E-Z-G)_n$;

(b) 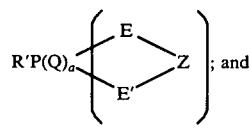; and (c) $R''_2P(Q)_aXP(Q)_aR''_2$ wherein E, E', G, R, R', R", Q, X, Z, a and n are as hereinbefore defined.

The proportions of the catalyst components can vary quite widely depending on the particular materials used and the absolute concentrations of the components. However, in general for each molecular proportion of component (1), there may be present from 0.05 to 20 molecular proportions of component (2), and from 0.01 to 10 molecular proportions of component (3) with the amount of component (3) not being greater than the amount of component (2). For polymerisation to high yields we preer to use 1 to 20 molecular proportions of component (2) and 0.1 to 4.0 molecular proportions of component (3).

In the phosphorus compounds the group R and R" attached to a given phosphorus atom are conveniently the same. In compound (c), it is particularly convenient if all the groups R" are the same. The groups R, R' and R" can be alkylamino groups —NR"'$_2$ wherein R"' is an alkyl group such as methyl or ethyl. Alternatively, the groups R, R' and R" may be a heterocyclic group such as pyridyl, pyrrolyl, pyrrolidyl or piperidyl and may be attached to the phosphorus atom through a carbon or nitrogen atom. If R or R" is a group (E—Z—G), this can be, for example an alkyl glycol; an alkanolamino, a diamino or an aminothiol group and G can be derived from a heterocyclic compound such as pyridine, quinoline, isoquinoline, etc. If both of the groups R" attached to the same phosphorous atom together form a group

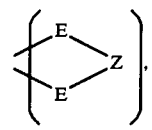

this can be the divalent residue from a glycol, an aminoalcohol, a diamine or an aminothiol. In compound (b) it is preferred that a is one and the group Q is oxygen. Conveniently, but not necessarily, in compound (c), the value of each a is the same, that is both are either zero or preferably one, and similarly it is preferred that both of the groups Q are the same and are oxygen.

In compound (b), it is preferred that at least one of the groups E and E' is —NR"'—, and it will be appreciated that the group

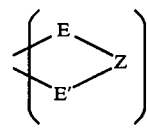

will not be the residue from a glycol since we have found that compounds containing such a group give poor results. If a is zero, that is when the phosphorus is trivalent it is preferred that group R' is (E—Z—G).

In compound (c), the group X can be derived from a monoamine or an acyclic or cyclic diamine. If the group X is of the type —NR"'(CH$_2$)$_m$NR"'—, the group R"' is preferably a hydrocarbyl group such as methyl and m is preferably 2 or 3. If the group X is of the type

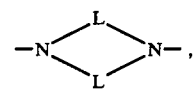

it is preferred that the groups L are both the same and are alkylene groups of the type —(CH$_2$)$_m$—, particularly ethylene groups when Z is derived from piperazine. We have obtained satisfactory polymerisation systems using as the phosphorus compound (c), materials in which the group X is

—N(CH$_3$)CH$_2$CH$_2$N(CH$_3$)—;

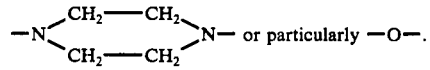

or particularly —O—.

In compound (c) when each a is zero it is preferred either that X is derived from an acyclic or cyclic diamine or that at least one R" is a group (E—Z—G).

Phosphorus compounds which may be used as the third component of the catalyst include compounds of the formulae I to XIX

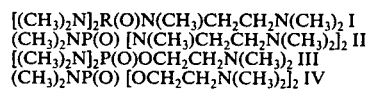

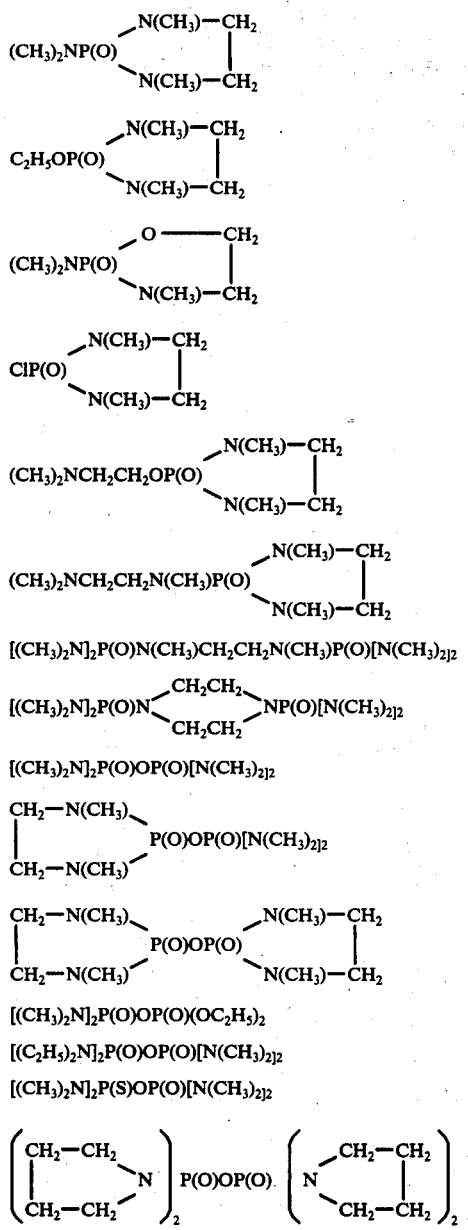

As a further aspect the present invention also includes an olefine polymerisation process which comprises polymerising at least one olefine monomer using an olefine catalyst in accordance with the present invention.

More particularly an olefine monomer is polymerised using a catalyst comprising (1) a solid compound of a transition metal wherein the said metal has a valency below its maximum, preferably titanium trichloride, (2) an organo-metallic compound of aluminium or of a non-transition metal of Group II of the Periodic System, or a complex of an organo-metallic compound of a non-transition metal of Group I or II of the Periodic System and an organo-aluminium compound and is particularly an aluminium hydrocarbyl halide; an aluminium hydrocarbyl sulphate; an aluminium hydrocarbyl oxhyydrocarbyl or preferably an aluminium trihydrocarbyl or aluminium dihydrocarbyl halide or hydride compound especially aluminium triethyl or aluminium diethyl chloride and (3) at least one phosphorus compound selected from materials of the formulae (a) $R_{3-n}P(Q)E-Z-G)_n$;

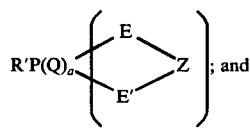

(c) $R\Delta_2P(Q)_aXP(Q)_aR\Delta_2$ where E, E', G, R, R', R", Q, X, Z, $a$ and $n$ are all as hereinbefore defined.

The phosphorus compound may be a compound of formulae I to XIX as hereinbefore defined.

Any olefine monomer which is capable of being polymerised using a Ziegler catalyst may be polymerised using the process of the present invention. Thus, olefine monomers which may be polymerised by the present process include butene-1 and 4-methyl pentene-1 and particularly propylene. The olefines may be copolymerised either together or with ethylene, conveniently using a sequential polymerisation process as described in British Pat. Nos. 970 478 and 1 014 944.

We have found that the present process can be used for the polymerisation of propylene to give a high rate of polymerisation and a relatively low proportion of soluble polymer.

Thus, if propylene at a partial pressure of one atmosphere is polymerised using a catalyst comprising titanium trichloride, aluminium triethyl and a phosphorus compound of formulae I to XIX, after 2½ hours the yield of solid polymer obtained can be in excess of 20 gms or even more than 30 gms of polymer/millimole of $TiCl_3$ in the catalyst with the amount of soluble polymer produced being less than 15%, or even less than 10%, by weight of the total polymer. Without the phosphorus compound and under otherwise the same conditions the yield of solid polymer is about 31.5 gms/millimole of $TiCl_3$, but the amount of soluble polymer is about 28.5% by weight. Thus, the addition of the phosphorus compound has produced a substantial reduction in the proportion of soluble polymer produced to give a more acceptable proportion of soluble polymer. In many cases, the rate of polymerisation is also somewhat reduced by the addition of the phosphorus compound, but this reduction in rate is not such as to render the catalyst too inactive for satisfactory use, and indeed in some cases the phosphorus compound actually increases the yield of the desired solid polymer, for example such an effect is obtained using a compound of formula V which gives a yield of about 39 gms/millimole of $TiCl_3$ under certain circumstances coupled with about 6% of soluble polymer. A rate in excess of 30 gms/millimole of $TiCl_3$ coupled with less than 10% of soluble polymer can also be obtained with a compound of formula III. Rates in excess of 25 gm/millimole of $TiCl_3$ coupled with less than 10% of soluble polymer can be obtained with compounds of formulae I, VI, XIII and XIV whilst at lower rates, less than 10% of soluble polymer can be obtained with compounds of formulae II, VII, VIII, IX, X, XII, XV and XVIII.

The titanium trichloride used in the foregoing tests was the reduction product of titanium tetrachloride with aluminium. It has been found that the polymerisation rate and proportion of soluble polymer formed is dependent on the nature of titanium trichloride used and although the use of the reaction product of titanium tetrachloride and aluminium alkyl sesquihalide can give a higher yield of solid polymer, a higher proportion of soluble polymer is also obtained with such catalysts.

The proportion of the phosphorous compound also effects the rate of polymerisation and proportion of soluble polymer produced. Furthermore, the effect of the phosphorus compound is dependent on the valency of the central phosphorus atom or atoms. If the phosphorus compound is a compound of trivalent phosphorus, that is a compound of formula

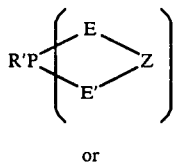

or

the effect of the phosphorus compound is dependent on the number of heteroatoms (that is O, S, N or P, other than the central phosphorus atom or atoms) present in the compound and in particular we have found that compounds containing O and/or N usually complex more strongly with the organo-metallic compounds such as organo-aluminium compounds than with titanium. Thus, using an organo-aluminium compound, the number of functional groups containing O and/or N should not exceed the amount of the aluminium compound and usually should be kept considerably less, for example, 0.25 to 0.5 of the amount of the aluminium compound. However, using the trivalent phosphorus compound in an amount such that the ratio of functional groups to Ti is <0.25 does not produce the best catalyst. Thus, the minimum proportion of the phosphorus compound is dependent on the titanium concentration and the upper limit is related to the concentration of the aluminium compound. More specifically, if the trivalent phosphorus compound contains $f$ functional groups (that is O or N) per molecule, the concentration of titanium trichloride is $C_T$ millimoles/liter and the concentration of aluminium triethyl is $C_A$ millimoles/liter, the concentration of the trivalent phosphorus compound is preferably in the range $$\frac{C_T}{4f} \text{ to } \frac{C_A}{2f} \text{ millimoles/liter}$$

Thus, if the basic catalyst system comprises 2 millimoles/liter of TiCl₃ and 4 millimoles/liter of aluminium triethyl, the concentration of a trivalent phosphorus compound containing 2 functional groups (that is, O or N atoms) per molecule is preferably in the range 0.25 to 1 millimole/liter and for a trivalent phosphorus compound containing 4 functional groups, the concentration is preferably in the range 0.125 to 0.5 millimole/liter.

If however the phosphorus compound is a compound of pentavalent phosphorus or, in the case of phosphorus compounds of formula (c), contains at least one pentavalent phosphorus atom, it is believed that the effect of such a compound is primarily affected by the group P(Q). Thus the number of groups P(Q) should not exceed the amount of organo-metallic compound, e.g., organo-aluminium compound, and usually should be a little less than the amount of the organo-metallic compound, preferably, when the organo-metallic compound is an organo-aluminium compound, not more than 0.75 of the molar proportion of aluminium compound. With such phosphorus compounds, if used in an amount such that the ratio of groups P(Q) to Ti to <0.1, this system does not produce the best catalyst. Thus, if the phosphorus compound contains $f$ groups P(Q) per molecule, the concentration of titanium trichloride is $C_T$ millimoles/liter and the concentration of aluminium triethyl is $C_A$ millimoles/liter, the concentration of the phosphorus compound is preferably in the range $$\frac{C_T}{10f} \text{ to } \frac{3C_A}{4f}$$

Thus, if the basic catalyst system comprises 2 millimoles/liter of TiCl₃ and 4 millimoles/liter of aluninium triethyl, the concentration of phosphorus compound containing one group P(Q) per molecule (that is any of compounds I to X), is preferably in the range 0.2 to 3.0 millimoles/liter. However, if the phosphorus compound contains two groups P(Q) per molecule (that is any of compounds XI to XIX), it is preferred that the concentration of the phosphorus compound is in the range 0.1 to 1.5 millimoles/liter.

Catalysts in accordance with the present invention can be used to prepare a large proportion of polymer for the use of a small quantity of catalyst. As is well known, catalysts of the "Ziegler" type are susceptible to the effects of impurities and the activity and stereospecificity of such catalysts can be affected in a detrimental manner by the presence of small quantities of impurities, particularly oxygen and polar compounds such as water and alcohol in the monomer and/or diluent when used. Thus, for the polymerisation of olefine monomers using Ziegler catalysts, it is known to use pure monomers and diluents. However, when using catalysts in accordance with the present invention, these can be used in smaller proportions than the conventional Ziegler type catalyst and accordingly are more susceptible to any impurities present in the system. Thus, for use with the catalyst of the present invention, we prefer that the monomers and any diluents are subjected to a further purification procedure.

Any suitable purification treatment can be used and the treatment can be effected in more than one stage if desired. The particular purification treatment used will be dependent on the purity of the starting materials.

Satisfactory purity can be achieved in most cases by passing the monomer (and diluent, if used) through a bed of a maerial which is capable of absorbing the impurities contained in the monomer of diluent, for example as described in British Pat. Specifications Nos. 1 111 493 and 1 226 659.

Using catalysts in accordance with the present invention, polymerisation can be carried out in the presence or absence of an inert diluent such as a suitably purified paraffinic hydrocarbon. If a diluent is not used, polymerisation can be effected in the liquid phase using excess liquid monomer as the suspension medium for catalyst and polymer product. If the monomer is used in the gaseous phase, polymerisation can be effected using any technique suitable for effecting a gas/solid reaction such as a fluidised bed reactor system.

The activity of the catalyst system can be increased by the use of the solid compound of the transition metal in a finely divided form. It is convenient to produce the transition metal compound in a finely divided form by grinding and particularly by ball-milling dry, for example as described in British Pat. Specifications Nos. 852 691 and 927 785.

A further improvement in the catalyst systems of the present invention can be obtained by grinding the transition metal compound together with an additional compound whch can be a phosphorus compound selected from materials of the formulae (a), (b) and (c) (as defined), or an electron donor compound of the type which is effective to alter the activity and/or stereo-specificity of the catalyst system. A wide range of such electron donors have been proposed which have such an effect and these include cyclic and acyclic amines such as pyridine, quinoline and triethylamine; diamines; alkanolamines; amides; urea and derivatives thereof; organo-phosphorus compounds such as phosphines, phosphites and phosphates; ethers; esters; ketones; alcohols and the sulphur containing analogues of such compounds such as thioethers etc; and silicon compounds such as silanes and siloxanes.

We have found that a further improvement in the catalyst can be obtained if a further quantity of the additional compound is included together with the product obtained by grinding the transition metal compound and the additional compound. The additional component ground with the transition metal compound can be the same as, or different from, the additional component which is added subsequently but it will be appreciated that the catalyst will include a phosphorus compound selected from materials of the formulae (a), (b) and (c) (as defined) and may include one or more of the electron donor compounds.

We particularly prefer to use catalyst systems in which the transition metal compound has been ground and especially when the grinding has been effected in the presence of an additional compound. The grinding can be effected at room temperature but higher or lower temperatures can be used if desired. If the transition metal compound has been ground with an additional compound at an elevated temperature, for example 60° C, it may be desirable to use the milled transition metal compound as a polymerisation catalyst shortly after being milled since if the transition metal compound is not used shortly after milling, the advantages of the hot milling are not fully achieved in all cases.

If a further quantity of an additional compound is incorporated in a catalyst system which includes a transition metal compound which has been ground with an additional compound, it is desirable that this further quantity of additional compound is not allowed to contact the transition metal compound in the absence of at least some of the organo-metallic compound which is component (2) of the catalyst. Indeed with the exception of the grinding process, it is generally preferred that the transition metal compound is not allowed to contact the phosphorus compound or the electron donor compound in the absence of the organo-metallic compound. The grinding of the transition metal compound and the phosphorus compound or electron donor compound is desirably effected using a molar excess of the transition metal compound, for example a molar ratio of transition metal compound phosphorus compound or electron donor compound of 6:1, 9:1, 12:1 or 18:1 although larger or smaller ratios may be used.

According to a further aspect of the present invention there is provided an olefine polymerisation catalyst comprising (1) a solid compound of a transition metal wherein the said metal has a valency below its maximum (2) an aluminium trihydrocarbyl; an aluminium dihydrocarbyl hydride, an aluminium hydrocarbyl halide, an aluminium hydrocarbyl sulphate or an aluminium hydrocarbyl oxyhydrocarbyl; and (3) at least one phosphorus compound selected from materials of the formulae (a) $R_{3-n}P(Q)(E-Z-G)_n$;

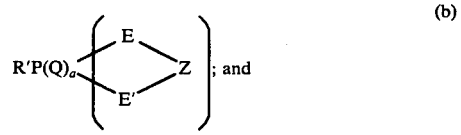

(c) $R''_2P(Q)_aXP(Q)_aR''_2$ where E, E', G, R, R', R'', Q, X, Z, $a$ and $n$ are as hereinbefore defined and the solid transition metal compound (1) has been modified by effecting grinding, preferably dry ball-milling, of the transition metal compound (1) with at least one additional compound which is either a phosphorus compound selected from materials of the formula (a) $R_{3-n}P(Q)(E-Z-G)_n$;

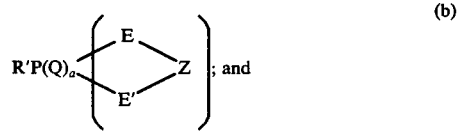

(c) $R''_2P(Q)_aXP(Q)_aR''_2$ or an electron donor compound which is effective to alter the activity and/or stereospecificity of the catalyst system.

As a further aspect of the present invention there is provided an olefine polymerisation catalyst comprising (1) a solid compound of a transition metal wherein the said metal has a valency below its maximum; (2) an aluminium trihydrocarbyl, an aluminium dihydrocarbyl hydride, an aluminium hydrocarbyl halide, an aluminium hydrocarbyl sulphate or an aluminium hydrocarbyl oxyhydrocarbyl; (3) at least one phosphorus compound selected from materials of the formulae (a) $R_{3-n}P(Q)(E-Z-G)_n$;

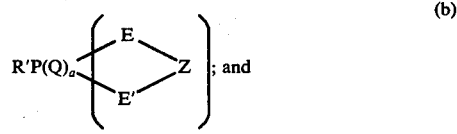

(c) $R''_2P(Q)_aXP(Q)_aR''_2$ where E, E', G, R, R', R'', Q, X, Z, $a$ and $n$ are as hereinbefore defined and optionally (4) an electron donor compound which is effective to alter the activity and/or stereospecificity of the catalyst system wherein the transition metal compound (1) has been modified by effecting grinding, preferably dry ball-milling, of the transition metal compound (1) with at least one addition compound which is either at least one phosphorus compound (3), (a), (b) or (c) or the electron donor compound (4) or both a phosphorus compound (3) (a), (b) or (c) and the electron donor compound (4) and the catalyst includes an amount of at least one compound from the group of the phosphorus compound (3) (a), (b) or (c) and the electron donor compound (4) which is in addition to that ground with the transition metal compound and which is not allowed to contact the modified transition metal compound in the absence of at least some of the organo-metallic compound (2), wherein the compound ground with the transition metal compound is the same as, or different from, the additional amount of compound and at least one of said compounds is a phosphorous compound selected from materials of the formulae (a) $R_{3-n}P(Q)(E—Z—G)$;

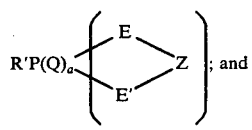; and (c) $R''_2P(Q)_a XP(Q)_a R''_2$

A particularly preferred catalyst of this type is one is which the transition metal compound has been ground with a phosphorus compound of formula (a) or (c) and the catalyst also includes an amount of a compound of the type (b). In particular the transition metal compound may be group with compound I or XIII and include an amount of compound V.

Electron donors which may be used to modify the catalyst have been extensively described in the literature and the choice of a suitable electron donor can be made from those which have been described, although it will be realised that the effect of and the optimum conditions for using an electron donor will depend on the particular electron donor selected. Catalyst systems including electron donor compounds or complexes including electron donors are disclosed inter alia in British Pat. Specification Nos. 803 198; 809 717; 880 998; 896 509; 920 118; 921 954; 933 236; 940 125; 966 025; 969 074; 971 248; 1 013 363; 1 049 723; 1 122 010; 1 150 845 and 1 208 815, Dutch Patent Application 70 15555 and German Pat. application No. 2 130 314.

It will be realised that there are many catalyst systems within the present invention and that the effectiveness of these catalyst will vary in dependence on the components of the catalysts and the relative proportions of the various components, and also on any special treatment, such as grinding, to which at least part of the catalyst may be subjected. It will also be appreciated that the catalyst may include in addition to at least one phosphorus compound of formula (a), (b) or (c), an electron donor compound and in such a system it is not necessary to grind the transition metal compound with either the phosphorus compound or the electron donor compound. The electron donor compound may be any of the types of compounds previously mentioned or may be an essentially nonpolar compound such as a cyclic polyene, particularly one in which the ring contains 7 or 8 carbon atoms such as cycloheptatriene, cyclooctatriene or cyclooctatrene.

Many of the phosphorus compounds used in the catalysts of the present invention are not believed to have been disclosed previously. Thus, as a further aspect of the present invention there is provided a new phosphorus compound having the formula (a) $R_{3-n}P(Q)(E—Z—G)$;

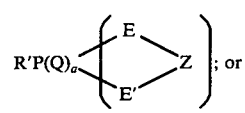; or (c) $R''_2P(Q)_a XP(Q)_a R''_2$ wherein
each R group is, independently, halogen, a hydrocarbyl group, a group $—NR''_2$ or $—OR''$ or a heterocyclic group;
R' is halogen, a hydrocarbyl group, a group $—NR''_2$, or $—OR'''$, a heterocyclic group or a group (E—Z—G);
R'' is halogen, a hydrocarbyl group, a group $—NR'''_2$ or $—OR'''$, a heterocyclic group, a group (E—Z—G) or both the R'' groups attached to the same P atom together form a group

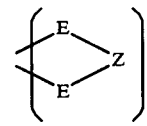

R''' is a hydrocarbyl group;
X is $—O—$, $—NR'''—$; $—E(CH_2)_m E—$ or

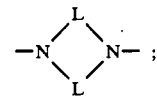

R'''' is hydrogen or R''';
L is a bivalent hydrocarbyl radical and each L may be the same or different;
each E is $—O—$, $—S—$ or $—NR'''—$ and may be the same or different;
E' is $—S—$ or $—NR'''—$;
G is $—OR'''$, $—SR'''$, $—NR'''_2$, $—PR'''_2$ or a heterocyclic ring system whereof the heteroatom is O, S, N or P;
Q is an oxygen or sulphur atom;
Z is a bivalent hydrocarbyl radical such that E and G, or E and E' or E and E are separated by not more than 3 carbon atoms;
each $a$ is independently zero or 1;
$m$ is a positive integer; and
$n$ is 1, 2 or 3 with the exceptions that when $n$ is 1 or 2, not all the groups R are $—OR''$ groups; when a is 1 and Q is oxygen the group R' is the group (E—Z—G) or a heterocyclic group and wherein each a is one and each R'' is attached to the same phosphorus atom are both $—NR'''_2$ or $—OR'''$, X is not $—O—$ or $—NR'''—$.

More specifically there are provided as new materials compounds having the formula I, II, III, IV, IX, X, XI, XII, XIV, XV, and XIX.

The present invention further provides methods of preparation of the new phosphorus compounds.

Thus, according to a further aspect of this invention, compounds of the type $R_{3-n}P(Q)(E—Z—G)_n$ where E, G, R, Q, Z and n are as defined with the exception that when n is 1 or 2, not all the groups R are —OR''' where R''' is as defined, are prepared by reaction of a compound H(E—Z—G) or a salt thereof, particularly an alkali metal salt and a phosphorus compound

R₃P(Q)

wherein at least one of the groups R is —NR'''₂, —OR''' or halogen and not all the groups R are —OR'''. Preferably the phosphorus compound is of the type R₃₋ₙP(Q)(Ha)ₙ where Ha is halogen, preferably chlorine. As a further aspect, compounds of the type

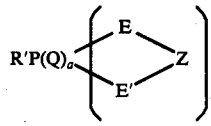

where E, E', R', Q, Z and a are as defined with the exception that when a is 1 and Q is oxygen the group R' is the group (E—Z—G) are prepared by the reaction of a compound H₂(E—Z—E') or a salt thereof, particularly the alkali metal salt and a phosphorus compound R'P(Q)ₐ(Ha)₂ where Ha is halogen, preferably chlorine. Alternatively, compounds of the type

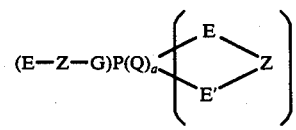

can be prepared by the reaction of a compound

H(E—Z—G)

or a salt thereof, particularly the alkali metal salt and a phosphorus compound

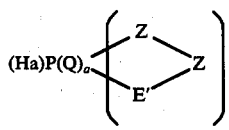

where Ha is as defined.

As yet a further feature of the present invention, phosphorus compounds of the type

R''₂P(Q)ₐX'P(Q)ₐR''₂ wherein R'', Q and a are as defined and X' is

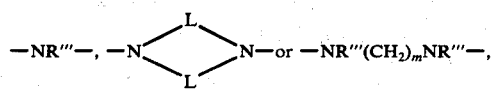

are prepared by the reaction of a compound H₂X' where X' is as defined and both hydrogen atoms and directly linked to nitrogen atoms, and a phosphorus compound R''₂P(Q)ₐ(Ha) where R, Q and a are as defined and Ha is halogen, particularly chlorine.

As yet a further feature of the present invention, phosphorus compounds of the type R''₂P(Q)ₐXP(Q-)ₐR''₂ wherein both the R'' groups attached to at least one of the phosphorus atoms together form a group

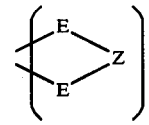

can be prepared by contacting a compound of the type

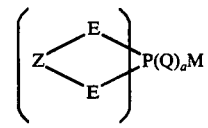

with a compound of the type

R''₂P(Q)ₐM wherein E, R'', Q, Z and a are as hereinbefore defined and M is a group OR''' in one compound and a halogen atom (Ha) in the other compound.

If both groups R'' on both phosphorus atoms together form a group

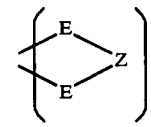

such compounds are prepared by contacting a compound of the type

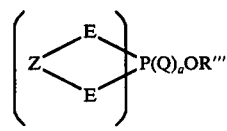

with a compound of the type

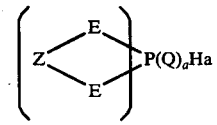

wherein E, R''', Q, Z, Ha and a are all as hereinbefore defined. Compounds of the type

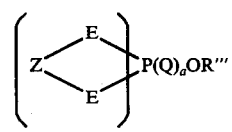

can be obtained as described in J. Org. Chem., 32 (1967) pages 1360 to 1362.

Compounds of the type

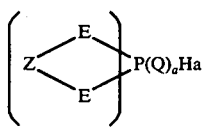

are preferably prepared by the reaction of P(Q)$_a$(Ha)$_3$ and H$_2$(E—Z—E) in the presence of pyridine as a diluent. Compounds of the type

R''$_2$P(O)OP(O)R''$_2$ are conveniently prepared using the procedure of our copending British patent application No. 30502/72. More specifically a compound

R''$_2$P(O)OP(O)R''$_2$ is prepared by contacting a compound

R''$_2$P(O)Ha with a urea derivative of the formula

R'NH)$_2$CO where R' is an alkyl group.

The preparation of the various phosphorus compounds using the process specified can be carried out in an inert diluent such as benzene, petroleum ether or diethyl ether or in the absence of a diluent, in an inert atmosphere such as argon or nitrogen, at a reaction temperature ranging from 0° C up to the boiling point of the diluent, or the boiling point of the mixture of reactants, which can be up to at least 240° C depending on the reactants. A convenient reaction temperature is in the range 0° to 100° C. In most cases the reaction occurs with the displacement of the groups R or Ha from the phosphorus compound as HR or HHa or the corresponding metal derivative. The extent of the reaction can be measured by titration of the displaced compound if it is basic, e.g., an amine, or by fractional distillation and collection, e.g., where the displaced compound is ethanol. If the displaced compound is acidic the reaction is preferably carried out in the presence of a compound which reacts with the acid to neutralize it, for example, if the displaced compound is a hydrogen halide the reaction can be carried out in the presence of a basic compound such as amine, particularly a tertiary monoamine, and the amine hydrohalide thus formed is removed by filtration before separating the phosphorus compound. Alternatively the displaced compound can be removed from the system as it is formed by the use of a continuous stream of an inert gas such as nitrogen. In some cases the reaction may proceed with the formation of a mixture of phosphorus compounds and it is usually possible to separate these compounds by distillation under reduced pressure.

Phosphorus compounds of formulae I to XIX have been characterised by boiling point, density, refractive index and melting point. The nuclear magnetic resonance data and the mass spectrum of the compounds was consistent with the formulae attributed to these materials.

The following Examples are illustrative of the various aspects of the present invention.

EXAMPLE 1

Preparation of [(CH$_3$)$_2$N]$_2$P(O)N(CH$_3$)CH$_2$CH$_2$N(CH$_3$)$_2$ 25 g (0.245 mole) N,N,N'-trimethylethylenediamine (CH$_3$NHCH$_2$CH$_2$N(CH$_3$)$_2$) and 24.8 g (0.245 mole) triethyl amine were charged into a 500 mls three-necked flask fitted with a stirrer, condenser, dropping funnel and nitrogen inlet. 150 mls of benzene was charged into the flask and the reaction mixture blanketed in nitrogen. A solution of 41.7 g (0.245 mole) bis(dimethylamino)-chlorophosphine oxide ([(CH$_3$)$_2$N]$_2$P(O)Cl.) in 50 mls benzene was then added to the contents of the flask. The reaction mixture was heated to reflux temperature (about 80° C) and maintained at this temperature for five hours after which heating was ceased and the mixture was allowed to cool. Triethylamine hydrochloride was filtered off, washed with dry benzene and the washings added to the main bulk of the filtrate. The benzene was removed by evaporation in a rotary evaporator under reduced pressure (60 mm) and the liquid residue fractionally distilled under reduced pressure. The fraction distilling between 119°–120° at 1.0 mm was collected and subjected to analysis and characterisation. The yield of this fraction, which was identified as [(CH$_3$)$_2$N]$_2$P(O)N(CH$_3$)CH$_2$CH$_2$N(CH$_3$)$_2$, was 52% based on the original phosphorus compound.

EXAMPLE 2

Preparation of (CH$_3$)$_2$NP(O)[N(CH$_3$)CH$_2$CH$_2$N(CH$_3$)$_2$]$_2$. 25 g (0.244 mole) N, N, N'-trimethylethylenediamine and 25 g (0.247 mole) triethylamine were dissolved in 170 mls benzene and charged, under nitrogen, into a 500 ml three-necked flask fitted with a stirrer, condenser and dropping funnel. The reaction mixture was blanketed with dry nitrogen. 19.85 g (0.122 mole) dimethylaminodichlorophosphine oxide ((CH$_3$)$_2$NP(O)Cl$_2$) in 30 mls benzene was added, dropwise and with stirring, to the contents of the flask at a rate such that the reaction was maintained under control. The addition was completed in 30 minutes and the reaction mixture was then heated to reflux (about 80° ) for 30 minutes. Triethylamine hydrochloride was filtered off, washed with dry benzene and the washings combined with the main filtrate. The benzene was removed by evaporation in a rotary evaporator under reduced pressure (60 mm) and the residual liquid fractionally distilled under reduced pressure. The fraction distilling at 140° C (0.5 mm) was collected and subjected to analysis and characterisation which was consistent with the material being of the formula (CH$_3$)$_2$NP(O)[N(CH$_3$)CH$_2$CH$_2$N(CH$_3$)$_2$]$_2$.

EXAMPLE 3

Preparation of [(CH$_3$)$_2$N]$_2$P(O)OCH$_2$CH$_2$N(CH$_3$)$_2$. 6.7 g (0.29 mole) sodium was cut into small pieces under petroleum ether (40–60) and added under a stream of dry nitrogen to 200 ml, N,N-dimethylethanolamine contained in a 500 ml three-necked flask fitted with a stirrer, condenser and dropping funnel. When all the sodium had reacted the excess dimethylethanolamine was removed by vacuum distillation at 30° C and 0.1 to 0.5 mm. 100 mls of dry benzene were added to the solid residue which was thus dissolved. The reaction mixture was cooled in an ice bath and a solution of 50.0 g (0.29 mole) of bis-dimethylamino)chlorophosphine oxide ([(CH$_3$)$_2$N]$_2$P(O)CL) in 50 ml benzene was added dropwise under nitrogen. On completion of the addition the reaction mixture was warmed to room temperature and stirred for 1 hour. Sodium chloride was formed as a precipitate which was filtered off. The filtrate was evaporated in a rotary evaporator under reduced pressure (60 mm) and the residual liquid fractionally distilled under reduced pressure (1 mm). The fraction distilling between 86°–88° C was collected and identified as [(CH$_3$)$_2$N]$_2$P(O)OCH$_2$CH$_2$N(CH$_3$)$_2$. The product was isolated in 64.4% yield.

EXAMPLE 4

Preparation of (CH$_3$)$_2$NP(O)[OCH$_2$CH$_2$N(CH$_3$)$_2$]$_2$. 9.3 g (0.404 mole) sodium was cut into small pieces under petroleum ether (40-60) and added under a stream of dry nitrogen to 200 ml N,N-dimethylethanolamine contained in a 500 ml three-necked flask fitted with a stirrer, condenser and dropping funnel. When all the sodium had reacted the excess dimethylethanolamine was removed by vacuum distillation at 30° C and 0.1 to 0.5 mm. 100 mls of dry benzene was added to the solid residue which dissolved and the solution obtained was cooled in an ice bath. A solution of 32.7 g (0.202 mole) dimethylaminodichlorophosphine oxide ((CH$_3$)$_2$NP(O)Cl$_2$) in 50 ml dry benzene was added dropwise under nitrogen to the cooled reaction mixture. On completion of the addition the reaction mixture was warmed to room temperature and the sodium chloride which precipitated was filtered off. The filtrate was evaporated in a rotary evaporator under reduced pressure (60 mm) and the residual liquid fractionally distilled under reduced pressure. The fraction distilling at 134° C (1.0 mm) was collected and identified as (CH$_3$)$_2$NP(O)[OCH$_2$CH$_2$N(CH$_3$)$_2$]$_2$. The product was isolated in 21% yield.

Various characteristics of the products obtained in Examples 1 to 4 were determined and these are set out in Table 1.

TABLE 1

| Compound Reference (a) | Boiling Point (° C/mmHg) | Density at 20° C (g/cm$^3$) | Refractive Index at 20° C | NMR (b) | Mass Spectrum (b) |
|---|---|---|---|---|---|
| I | 120/1.0 mm | 1.013 | 1.468 | YES | YES |
| II | 140/0.5 mm | 1.004 | 1.472 | YES | YES |
| III | 86/1.0 mm | 1.03 | 1.450 | YES | YES |
| IV | 134/1.0 mm | 0.95 | 1.448 | YES | YES |

Notes to Table 1
(a) The compound references are as follows:
I product of Example 1, formula corresponds to Formula I,
II product of Example 2, formula corresponds to Formula II,
III product of Example 3, formula corresponds to Formula III,
IV product of Example 4, formula corresponds to Formula IV,
(b) YES means NMR or Mass spectrum consistent with formula given.

EXAMPLE 5

Preparation of

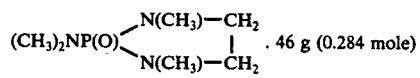 . 46 g (0.284 mole)

and 57.87 g (0.568 mole) triethylamine were dissolved, under nitrogen, in 100 mls benzene and charged into a 500 mls three-necked flask equipped with a condenser, stirrer and dropping funnel. 25 g (0.284 mole) N,N'-dimethylethylenediamine (CH$_3$NHCH$_2$CH$_2$NHCH$_3$) were dissolved in 50 mls benzene and gradually added, from a dropping funnel, into the reaction flask. The reaction was exothermic and heating of the reaction mixture was unnecessary. When the addition of the diamine had been completed, stirring of the reaction mixture was continued for 12 hours at room temperature (15°–20° C). Triethylamine hydrochloride was filtered off and washed with dry benzene and the washings combined with the main filtrate. The combined benzene solutions were evaporated in a rotary evaporator under reduced pressure (60 mm) and the residual liquid fractionally distilled under reduced pressure. The fraction distilling between 105°–106° C (3.0 mm) was collected. The yield of this fraction, which was identified as

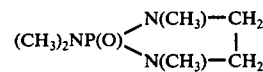

was 72.5% based on the original phosphorus compound.

EXAMPLE 6

Preparation of -

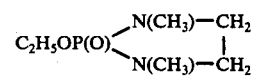

The procedure of Example 5 was repeated using 46 g (0.284 mole) ethyl phosphorodichloridate (C$_2$H$_5$OP(O)Cl$_2$) in place of dimethylaminodichlorophosphine oxide. The fraction distilling between 88°–90° C (0.2 mm) was collected in a yield of 58.4% based on the original phosphorus compound.

EXAMPLE 7

Preparation of

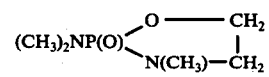

The procedure of Example 5 was repeated using 21.3 g (0.284 mole) N-methyl ethanolamine (CH$_3$NHCH$_2$CH$_2$OH) in place of N,N'-dimethylethylenediamine. The fraction distilling between 94°–95° C (0.2 mm) was collected in a yield of 76.2% based on the original phosphorus compound.

EXAMPLE 8

Preparation of

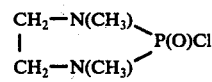

204.2 g(1.33 mole) phosphoryl chloride (POCl$_3$) and 400 mls pyridine were charged under a stream of dry nitrogen into a 1 liter three-neck flask fitted with a stirrer, condenser and dropping funnel. The mixture was cooled in an ice bath. A solution of 116.8 g (1.33 mole) N,N'-dimethyl-ethylenediamine was added dropwise under nitrogen. When the addition was complete the reaction mixture was warmed to room temperature and stirred at this temperature for 1 hour. Pyridine hydrochloride precipitated and was filtered off. The filtrate was evaporated in a rotary evaporator under reduced pressure (60 mm). The residual solid was distilled under reduced pressure and the fraction distilling at 100° C (0.5 mm) was collected. The yield of this fraction was 85.8% of the theoretical and the product was identified as

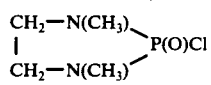

EXAMPLE 9

Preparation of

3.45 g (0.15 mole) sodium was cut into small pieces under petroleum ether (40–60) and added to 100 ml N,N-dimethylethanolamine under a dry nitrogen atmosphere. When all the sodium had dissolved the excess solvent was removed by vacuum distillation leaving a solid residue of the sodium salt of N,N-dimethylethanolamine. This sodium salt was dissolved in 50 mls benzene and the solution was charged to a dropping funnel and added dropwise to a suspension of 25.2 g (0.15 mole) 2-chloro-1,3-dimethyl-1,3,2-diaza-phospholidine-2-oxide

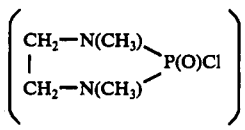

in 50 mls dry benzene contained in a 250 ml three-neck flask equipped with a stirrer, condenser and thermometer. The reaction was exothermic. On complete addition of the sodium salt the reaction mixture was heated for 1 hour under reflux, cooled and filtered. The filtrate was evaporated in a rotary evaporator under reduced pressure (60 mm) and the residual liquid fractionally distilled under reduced pressure. The fraction distilling between 124°–126° C (1.0 mm) was collected. The yield of this fraction was 35% of the theoretical and the product was identified as

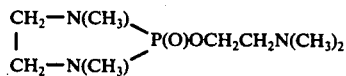

EXAMPLE 10

Preparation of

31.1 g (0.185 mole) 2-chloro-1,3-dimethyl-1,3,2-diazaphospholidine-2-oxide

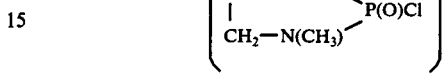

18.7 g (0.185 mole) triethylamine and 150 ml benzene were charged under a stream of dry nitrogen into a 500 ml three neck flask fitted with a stirrer, dropping funnel and condenser. A solution of 18.9 g (0.185 mole) N,N,N'-trimethylethylene diamine in 50 mls dry benzene was added dropwise, under nitrogen, to the reaction mixture. When the addition was complete the reaction mixture was heated under reflux for 1 hour. Solid triethylamine hydrochloride precipitated and was filtered off. The filtrate was evaporated using a rotary evaporator under reduced pressure (60 mm). The residual liquid was fractionally distilled under reduced pressure and the fraction distilling at 114° C (0.2 mm) was collected. The yield of this fraction was 35% of the theoretical and the product was identified as

TABLE 2

| Compound Reference (a) | Boiling Point °C/mmHG | Melting Point | Density g/ml 20° C | Refractive Index 20° C | NMR (b) | Mass Spectrum (b) |
|---|---|---|---|---|---|---|
| V | 90/0.8mm | | 1.14 | 1.475 | YES | YES |
| VI | 90/0.2mm | | 1.24 | 1.461 | YES | YES |
| VII | 95/0.2mm | | 1.162 | 1.465 | YES | YES |
| VIII | 100/0.5mm | 66–66.5 | — | — | YES | YES |
| IX | 124/1mm | | 1.10 | 1.469 | YES | YES |
| X | 114/0.2mm | | 1.05 | 1.479 | YES | YES |

NOTES to Table 2
(a) The compound references are as follows:
V product of Example 5, formula corresponds to Formula V
VI product of Example 6, formula corresponds to Formula VI
VII product of Example 7, formula corresponds to Formula VII
VIII product of Example 8, formula corresponds to Formula VIII
IX product of Example 9, formula corresponds to Formula IX
X product of Example 10, formula corresponds to Formula X
(b) YES means NMR or Mass spectrum consistent with formula given.

EXAMPLE 11

Preparation of
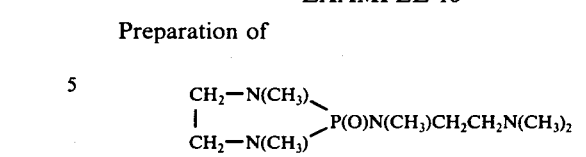

20.2 g (0.23 mole) NN'-dimethylethylenediamine (CH₃NHCH₂CH₂NHCH₃) and 46.4 g (0.46 mole) triethylamine were dissolved in 270 mls dry benzene and charged into a 500 ml three-necked flask fitted with a stirrer, condenser and dropping funnel. The reaction mixture was blanketed under nitrogen. To this solution was added, dropwise and with stirring, a solution of 76.7 g bis(dimethylamino)chlorophosphine oxide $[(CH_3)_2N]_2P(O)Cl$ in 30 ml benzene. The reaction mixture was heated under reflux at a temperature of 85° C for 30 hours. Triethylamine hydrochloride precipitated and was filtered off, washed with benzene and the washings added to the main filtrate. The benzene was removed by evaporation using a rotary evaporator under reduced pressure (60 mm) and the liquid residue fractionated under reduced pressure. The fraction distilling at 200° C (1 mm) was collected as a white solid. This fraction was identified as $[(CH_3)_2N]_2P(O)N(CH_3)CH_2CH_2N(CH_3)$-$P(O)[N(CH_3)_2]_2$ and was obtained in a 60% yield based on the amount of phosphorus compound starting material.

EXAMPLE 12

Preparation of

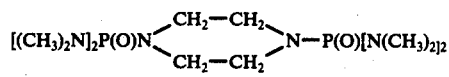

100.8 g. (1.172 mole) anhydrous piperazine was dissolved in 400 mls dry benzene and charged under a stream of dry nitrogen, into a 1 liter three-necked flask equipped with a stirrer, condenser and dropping funnel. The reaction mixture was blanketed under dry nitrogen for the duration of the synthesis. 200 g (1.231 mole) bis(dimethylamino)chlorophosphine oxide in 100 mls dry benzene was added, dropwise and with stirring, to the contents of the flask at such a rate as to maintain the temperature below 50° C. The reaction mixture was stirred at 50° C for 2 hours and then heated at reflux (85° C) for a further 30 minutes. Piperazine hydrochloride was filtered off and washed with dry benzene. The washings were added to the main filtrate and most of the benzene removed by evaporation using a rotary evaporator under reduced pressure (60 mm). The product crystallised from the benzene solution, was filtered off and recrystallised from dry benzene. MPt = 131°–132° C. The yield of product, based on the phosphorus starting material was 50% and was identified as the compound

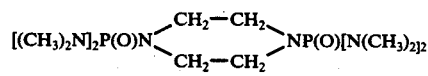

EXAMPLE 13

Preparation of $[(CH_3)_2N]_2P(O)OP(O)[N(CH_3)_2]_2$. A one liter 3-necked flask was fitted with a stirrer, condenser, dropping funnel, thermometer and nitrogen inlet. The flask was purged with nitrogen and in succession, 200 mls benzene, 22 gms (0.25 moles) of 1,3-dimethylurea, $((CH_3NH)_2CO)$ and 50.6 gms (0.50 moles) of triethylamine were introduced into the flask, the contents of which were heated to 60° C until the 1,3-dimethylurea had dissolved.

85.25 gms (0.50 moles) bis(dimethylamino)chlorophosphine oxide $([(CH_3)_2N]_2P(O)Cl)$ were added gradually to the flask and a precipitate started to form after 10 minutes addition. Since the reaction was not exothermic, the rate of addition of the phosphine oxide was increased. When the addition of the phosphine oxide had been completed (after 15 minutes), the contents of the flask were heated to reflux temperature (85° C) which was maintained for 4 hours. At the end of this time, heating was ceased and the reaction mixture allowed to cool. The solid triethylamine hydrochloride was filtered off, washed with benzene and dried.

The benzene was removed from the reaction product by evaporation in a rotary evaporator at reduced pressure (60 mm) and the solution was fractionally distilled. The fraction distilling at 130° C (at 0.8 mm) was collected and this material was identified as octamethylpyrophosphoramide $([(CH_3)_2N]_2P(O)OP(O)[N(CH_3)_2]_2)$ by mass spectrometry and nuclear magnetic resonance.

EXAMPLE 14

Preparation of

21.9 g (0.13 mole) bis-(dimethylamino)chlorophosphine oxide $([(CH_3)_2N]_2P(O)Cl)$ and 24.6 g (0.14 mole) 2-ethoxy-1,3-dimethyl-1,3,2-diazaphosphine-2-oxide

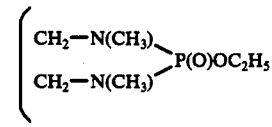

prepared from ethyl phosphorodichloridate $(C_2H_5OP(O)Cl_2)$ and N,N'-dimethylethylenediamine as described in J. Org. Chem. 32 (1967) pages 1360–1362) were charged under a stream of dry nitrogen, into a 100 ml three-necked flask equipped with a condenser, stirrer and thermometer. The reactants were heated to 170° C and maintained at this temperature until evolution of ethyl chloride ceased (about 20 minutes). The final reaction mixture was subjected to fractional distillation under reduced pressure and the fraction distilling at 138°–140° C (0.2 mm) was collected. This fraction was identified as

and was obtained in a 75% yield.

EXAMPLE 15

Preparation of

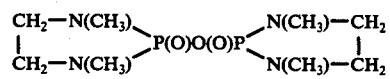

18.9 g (0.112 mole) 2-chloro-1,3-dimethyl-1,3,2-diazaphospholidine-2-oxide

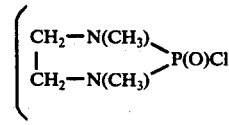

prepared from POCl$_3$ and N,N'-dimethylethylenediamine in the presence of pyridine as a solvent) and 20.9 g (0.117 mole) 2-ethoxy-1,3-dimethyl-1,3,2-diazaphospholidine-2-oxide

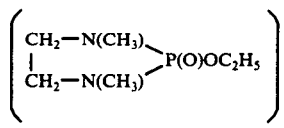

where charged under a stream of dry nitrogen, into a 100 ml 3-necked flask fitted with a stirrer, condenser and thermometer. The reactants were heated to 140° C and maintained at this temperature until evolution of ethyl chloride ceased. The final reaction mixture was subjected to fractional distillation under reduced pressure and the fraction distilling at 190° (3.5 mm) was collected. This fraction was identified as

and was obtained in 54% yield.

EXAMPLE 16

Preparation of

[(CH$_3$)$_2$N]$_2$P(O)O(O)P(OC$_2$H$_5$)$_2$ 34.5 g (0.2 mole) bis(ethoxy)chlorophosphine oxide ((C$_2$H$_5$O)$_2$P(O)Cl)

and 36.0 g (0.2 mole) N,N,N',N'-tetramethyl ethyl phosphorodiamidate ([(CH$_3$)$_2$N]$_2$P(O)OC$_2$H$_5$)

were charged under a stream of dry nitrogen into a 100 ml three-necked flask fitted with a stirrer, condenser and thermometer. The reactants were heated to 120° C and maintained at this temperature until evolution of ethyl chloride ceased. The final reaction mixture was subjected to fractional distillation and the fraction distilling between 120°–124° C (0.2 mm) was collected. This fraction was found to be mainly the required product, but with some contamination. After a further two fractional distillations, pure

[(CH$_3$)$_2$N]$_2$P(O)O(O)P(OC$_2$H$_5$)$_2$, distilling at 136° C (0.5 mm) was isolated in 39% yield.

EXAMPLE 17

Preparation of

[(CH$_3$)$_2$N]$_2$P(O)O(O)P[N(C$_2$H$_5$)$_2$]

27.18 g (0.12 mole) bis-(diethylamino)chlorophosphine oxide ([(C$_2$H$_5$)$_2$N]$_2$P(O)Cl)

and 21.6 g (0.12 mole) N,N,N',N'-tetramethyl ethyl phosphorodiamidate ([(CH$_3$)$_2$N]$_2$P(O)OC$_2$H$_5$)

were charged under a stream of dry nitrogen into a 100 ml three-necked flask fitted with a stirrer, condenser and thermometer. The reactants were heated to 170° C until evolution of ethyl chloride ceased. The final reaction mixture was fractionated and the fraction distilling at 180° C (3.0 mm) was collected. This fraction was identified as

[(CH$_3$)$_2$N]$_2$P(O)O(O)P[N(C$_2$H$_5$)$_2$]$_2$ and was obtained in 65% yield.

EXAMPLE 18

Preparation of

[(CH$_3$)$_2$N]$_2$P(O)O(S)P[N(CH$_3$)$_2$]$_2$ 29.9 g (0.15 mole) bis-(dimethylamino)thiophosphonyl chloride ([(CH$_3$)$_2$N]$_2$P(S)Cl)

and 27.03 g (0.15 mole) N,N,N',N'-tetramethyl ethyl phosphorodiamidate ([(CH$_3$)$_2$N]$_2$P(O)OC$_2$H$_5$)

were charged under a stream of dry nitrogen into a 100 ml three-necked flask fitted with a stirrer, condenser and thermometer. The reactants were heated to 170° C and maintained at this temperature until evolution of ethyl chloride ceased. The final reaction mixture was fractionated under reduced pressure and the fraction distilling at 134° C (0.3 mm) was collected. This fraction was identified as

[(CH$_3$)$_2$N]$_2$P(O)O(S)P[N(CH$_3$)$_2$]$_2$ and was obtained in 60% yield.

EXAMPLE 19

Preparation of

3.08 g (0.134 mole) sodium was dissolved in ethanol and the excess ethanol removed using a rotary evaporator. The sodium ethoxide produced above was charged under a stream of dry nitrogen into a 500 ml three-necked flask fitted with a stirrer, condenser and dropping funnel and 150 ml dry benzene was added.

A solution of 30 g (0.134 mole) bis-pyrrolidinochlorophosphine oxide

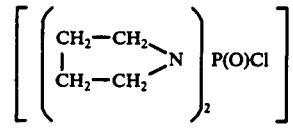

in 100 ml dry benzene (prepared as described hereafter) was added dropwise to the sodium ethoxide solution. On completion of the addition the reaction mixture was heated under reflux for 2½ hours and then cooled to room temperature. The precipitated sodium chloride was removed by filtration. The benzene was removed from the filtrate using a rotary evaporator at reduced pressure (60 mm) and the product was fractionally distilled under reduced pressure (0.5 mm). The fraction distilling at 225° C was collected. This fraction was identified as

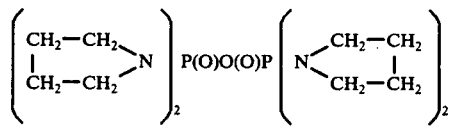

The bis-pyrrolidinochlorophosphine oxide was prepared as follows:

56.8 g (0.8 mole) pyrrolidine, 80.8 g (0.8 mole) triethylamine and 300 ml dry benzene were charged into a 1 liter three-necked flask equipped with a stirrer, condenser and dropping funnel. A solution of $POCl_3$ in 70 mls dry benzene was added dropwise under a stream of dry nitrogen. The reaction was exothermic. On complete addition of the $POCl_3$/benzene solution, the reaction mixture was stirred for 1½ hours at room temperature. The precipitated triethylamine hydrochloride was filtered off and the filtrate evaporated using a rotary evaporator under reduced pressure (60 mm). The product was fractionally distilled under reduced pressure (0.3 - 0.5 mm) and the fraction distilling between 138°-140° collected. This fraction was identified as

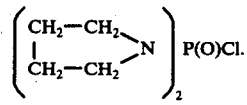

Various characteristics of the products obtained in Examples 11 to 19 were determined and these are set out in Table 3.

TABLE 3

| Compound Reference (a) | Boiling Point ° C/mmHg | Melting Point ° C | Density g/ml 20° C (c) | Refractive Index 20° C (c) | NMR (b) | Mass Spectrum (b) |
|---|---|---|---|---|---|---|
| XI | 200/1 mm | 43–44 | ND | ND | YES | YES |
| XII | ND | 131–132 | ND | ND | YES | YES |
| XIII | 136/0.8 mm | — | 1.15 | 1.464 | YES | YES |
| XIV | 138/0.2 mm | — | 1.20 | 1.475 | YES | YES |
| XV | 190/3.5 mm | 89–89.5 | — | — | YES | YES |
| XVI | 136/0.5 mm | — | 1.19 | 1.4415 | YES | YES |
| XVII | 180/3.0 mm | — | — | 1.464 | YES | YES |
| XVIII | 134/0.3 mm | — | — | — | YES | YES |
| XIX | 225/0.5 mm | ND | ND | ND | YES | YES |

(a) The compound references are as follows:
XI product of Example 11, formula corresponds to Formula XI
XII product of Example 12, formula corresponds to Formula XII
XIII product of Example 13, formula corresponds to Formula XIII
XIV product of Example 14, formula corresponds to Formula XIV
XV product of Example 15, formula corresponds to Formula XV
XVI product of Example 16, formula corresponds to Formula XVI
XVII product of Example 17, formula corresponds to Formula XVII
XVIII product of Example 18, formula corresponds to Formula XVIII
XIX product of Example 19, formula corresponds to Formula XIX
(b) YES means NMR and Mass spectrum consistent with formula given
(c) ND means not determined.

EXAMPLES 20 TO 32

The products of Examples 1 to 4 were used as olefine polymerisation catalyst third components. The effect of the phosphorus compounds was tested in propylene polymerisations using triethyl aluminium and a commercially available form of titanium trichloride manufactured by Toho Titanium Company of Japan and identified as TAC 131. (This material is believed to be obtained by the reduction of $TiCl_4$ with aluminium metal and thereafter ball-milling the dry powder).

A polymerisation flask equipped with efficient stirrer and a water jacket was dried carefully and 1 liter of an inert hydrocarbon diluent having a boiling range of about 170°-175° C was introduced. The diluent was evacuated at 60° C, purged with nitrogen and evacuated, which treatment effectively reduced the water and oxygen contents of the diluent to below 10 ppm by weight. The diluent was then saturated with propylene to one atmosphere pressure. The propylene used was obtained from propylene containing methylacetylene and allene impurities well below 10 ppm which had been further purified by passage through a column of activated alumina at 50° C. Triethyl-aluminium was introduced in the proportions indicated in Table 4 followed by the phosphorus compound to be tested. After half hour 2 millimoles of $TiCl_3$ were introduced. The pressure in the reaction vessel was maintained at one atmosphere by supply of propylene from a burette. After a further 2.5 hours the run was terminated with 10 ml of isopropanol and a sample of supernatant liquid extracted for determining the concentration of soluble polymer. The solid was filtered and washed three times with petrol ether and dried in a vacuum oven at 120° C for an hour. The yield of solid plus calculated soluble polymer equalled within experimental error the propylene lost from the burette.

The results obtained are set out in Table 4.

Comparative examples (Examples A and B) were carried out in a similar manner but omitting the phosphorus compound.

TABLE 4

| Example or Comparative Example | Phosphorus Compound Reference | Phosphorus Compound Amount (mmol) | AlEt$_3$ (mmol) | Conversion to Solid (g/mmol Ti) (d) | Soluble Yield (%) (e) |
|---|---|---|---|---|---|
| 20 | I | 0.5 | 4 | 27.5 | 9.4 |
| 21 | I | 1.0 | 4 | 24 | 7.3 |
| 22 | I | 1.5 | 4 | 14.5 | 4.5 |
| 23* | I | 1.5 | 5 | 22.7 | 6.7 |
| 24* | I | 0.5 | 4 | 32.2 | 10.3 |
| 25* | I | 1.0 | 4 | 22.2 | 8.0 |
| 26* | II | 0.25 | 4 | 32.2 | 17 |
| 27* | II | 0.5 | 4 | 30 | 14.2 |
| 28* | II | 1.0 | 4 | 15.0 | 9.2 |
| 29* | III | 0.5 | 4 | 32.4 | 9.3 |
| 30* | III | 1.0 | 4 | 28.1 | 8.5 |
| 31* | IV | 0.25 | 4 | 30.8 | 17.0 |
| 32* | IV | 0.5 | 4 | 31.4 | 11.7 |
| A | none | — | 4 | 31.5 | 29.0 |

TABLE 4-continued

| Example or Comparative Example | Phosphorus Compound Reference | Amount (mmol) | AlEt₃ (mmol) | Conversion to Solid (g/mmol Ti) (d) | Soluble Yield (%) (e) |
|---|---|---|---|---|---|
| B* | none | — | 4 | 29.3 | 27.0 |

(d) Based on solid polymer only
(e) % based on total polymer (solid + soluble) formed.
*In these experiments the titanium trichloride was TAC 141 supplied by Toho Titanium Company of Japan.

EXAMPLES 33 to 51

The general procedure of Examples 20 to 32 was repeated using the products of Examples 5 to 10. The results obtained are set out in Table 5. In Table 5, * indicates that the titanium trichloride was TAC 141, in all other experiments the titanium trichloride was TAC 131.

EXAMPLES 52 to 69

The general procedure of Examples 20 to 32 was repeated using the products of Examples 11 to 19. The results obtained are set out in Table 6.

EXAMPLES 70 to 73

The effect of ball-milling the transition metal compound with a phosphorus compound was studied.

The milling was carried out in a steel mill 6 inches long and 3⅛ inches diameter using a mixture of 200 steel balls of ½ inch diameter and 200 steel balls of ¼ inch diameter. The transition metal compound was TAC 141 titanium trichloride supplied by Toho Titanium Company of Japan and the phosphorus compound was the product of Example 1. The two materials were introduced into the mill as a slurry in pentane, which was evaporated off before commencing the milling. The molar ratio TAC 141 to phosphorus compound was 9:1 and milling was effected at 120 rpm for 24 hours. A nitrogen atmosphere was maintained in the mill throughout.

TABLE 5

| Example or Comparative Example | Phosphorus Compound Reference | Amount (mmol) | AlEt₃ (mmol/l) | Conversion to Solid (g/mmol Ti) (d) | Soluble Yield (%) (e) |
|---|---|---|---|---|---|
| 33 | V | 1 | 4 | 30.5 | 8.6 |
| 34 | V | 2 | 4 | 38.8 | 5.9 |
| 35 | V | 3 | 4 | 27.5 | 5.1 |
| 36 | V | 4 | 5 | 17.8 | 5.1 |
| 37 | VI | 1 | 4 | 28 | 7.9 |
| 38 | VI | 2 | 4 | 23.8 | 6.1 |
| 39 | VI | 3 | 4 | 13.4 | 4.3 |
| 40* | VI | 1 | 4 | 27.7 | 8.4 |
| 41* | VI | 2 | 4 | 23.6 | 6.6 |
| 42* | VI | 3 | 4 | 14.2 | 4.7 |
| 43* | VI | 3 | 5 | 27.6 | 6.1 |
| 44 | VII | 1 | 4 | 19.2 | 6.9 |
| 45 | VII | 2 | 4 | 17.5 | 5.9 |
| 46* | VIII | 1.2 | 4 | 20.1 | 8.1 |
| 47* | VIII | 2.1 | 4 | 16.6 | 6.8 |
| 48* | IX | 0.5 | 4 | 26.3 | 11.0 |
| 49* | IX | 1.0 | 4 | 13.8 | 8.5 |
| 50* | X | 0.5 | 4 | 30.9 | 10.9 |
| 51* | X | 1.0 | 4 | 24.0 | 8.3 |
| A | none | — | 4 | 31.5 | 28.5 |
| B* | none | — | 4 | 29.3 | 27.0 |

TABLE 6

| Example or Comparative Example | Phosphorus Compound Ref (f) | Amount (mmol/l) | Conversion to solid (g/mmol Ti) (d) | Soluble Yield (%) (e) |
|---|---|---|---|---|
| 52 | XI | 0.5 | 28.2 | 12.8 |
| 53 | XI | 1.0 | 22 | 13.7 |
| 54 | XII | 0.5 | 27.7 | 12.7 |
| 55 | XII | 1 | 23 | 9.9 |
| 56 | XIII | 0.5 | 28.1 | 7.9 |
| 57 | XIII | 1.0 | 27.8 | 7.3 |
| 58* | XIV | 0.5 | 29.3 | 8.9 |
| 59* | XIV | 1.0 | 19.0 | 6.1 |
| 60* | XV | 0.5 | 32.9 | 10.2 |
| 61* | XV | 1.0 | 22.7 | 7.3 |
| 62* | XVI | 0.5 | 39.4 | 12.5 |
| 63* | XVI | 1.0 | 32.7 | 10.0 |
| 64* | XVII | 0.5 | 35.6 | 11.8 |
| 65* | XVII | 1.0 | 40.8 | 10.1 |
| 66* | XVIII | 0.5 | 25.25 | 10.0 |
| 67* | XVIII | 1.0 | 16.3 | 8.1 |
| 68** | XIX | 0.5 | 32.7 | 12.0 |
| 69** | XIX | 1.0 | 28.7 | 11.0 |
| A | None | — | 35 | 29.0 |
| B* | None | — | 29.3 | 27.0 |
| C** | None | — | 32.5 | 29.3 |

*In these experiments the titanium trichloride was TAC 141, in all other experiments the titanium trichloride was TAC 131.
**In these experiments the titanium trichloride was Stauffer AA.

In Example 70, polymerisation was carried out as described in Examples 20 to 32 with the exception that 8 millimoles of aluminium triethyl was used and no additional phosphorus compound was added other than that incorporated into the titanium trichloride by the milling. In further polymerisations which were carried out and which are set out as Examples 71 to 73, a further quantity of a phosphorus compound was used, this further quantity being added shortly after the aluminium triethyl and half an hour before adding the milled titanium trichloride.

The procedure used and results obtained are summarised in Table 7.

TABLE 7

| Example No. | Fourth Component Ref | Amount (mmol/l) | Conversion to solid polymer (g/mmol Ti) (d) | Soluble Yield (%) (e) |
|---|---|---|---|---|
| 70 | NIL | NIL | 56 | 6.8 |
| 71 | I | 1.5 | 51 | 4.2 |
| 72 | V | 3.0 | 48 | 4.6 |
| 73 | VI | 3.0 | 40 | 4.3 |

(d) (e) see Table 4.

EXAMPLES 74 to 76

The transition metal compound was ball-milled with an electron donor compoumd.

The transition metal compound was TAC 121 titanium trichloride supplied by the Toho Titanium Company of Japan and the electron donor was triphenyl phosphine oxide. The compounds were added directly to the mill in the solid form, the titanium trichloride being added first. The mill used was 9 inches long and 5.1 inches diameter and contained 685 steel balls of ½ inch diameter. The molar ratio of titanium trichloride to triphenyl phosphine oxide was 6:1 and milling was effected at 64 rpm for 65 hours. A nitrogen atmosphere was maintained in the mill at all times during loading, milling and unloading.

Polymerisation was carried out as described in respect of Examples 71 to 73 with the addition of quantities of phosphorus compounds of the type defined. A comparative example (Example D) was carried out in the absence of a further phosphorus compound. The results obtained are set out in Table 8.

TABLE 8

| Example or Comparative Example | Fourth Component Ref | Amount (mmol/l) | Conversion to solid polymer (g/mmol Ti) (d) | Soluble Yield (%) (e) |
|---|---|---|---|---|
| 74 | I | 1.5 | 50 | 4.1 |
| 75 | V | 2 | 63 | 6.3 |
| 76 | V | 5 | 64 | 3.8 |
| D | NIL | NIL | 75 | 11.4 |

(d) (e) see Table 4

EXAMPLES 77 to 79

30 gms of a sample of pure TiCl$_3$ produced by hydrogen-reduction of TiCl$_4$ were activated by milling under nitrogen in a stainless-steel mill 3 inches diameter, 6 inches long containing 200 half-inch and 200 quarter-inch stainless steel balls. The mill was rotated at 120 rpm for 24 hours.

Propylene was polymerised with this catalyst under conditions similar to those described in Examples 71 to 73. The results obtained and the catalyst systems used are set out in Table 9 together with a comparison example wherein the phosphorus compounds were omitted from the polymerisation.

TABLE 9

| Example or Comparative Example | Phosphorus Compound Ref | Amount (mmol/l) | Conversion to solid polymer (g/mmol TiCl$_3$) (d) | Soluble Yield (%) (e) |
|---|---|---|---|---|
| 77 | I | 1.5 | 21 | 8.7 |
| 78 | V | 3 | 25 | 9.5 |
| 79 | VI | 3 | 21.5 | 7.15 |
| E | None | | 23 | 28.3 |

(d) (e) see Table 4

If the unmilled titanium trichloride is used, in the absence of a phosphorus compound, in a polymerisation process as described in Example 20 to 32 the yield of solid polymer is about 2.5 gms/millimole Ti and about 25 to 28% of soluble polymer.

EXAMPLES 80 and 81

The effect of ball-milling the transition metal compound with a different phosphorus compound of the type defined was studied.

The milling was carried out in the same ball-mill as in Examples 70 to 73. The transition metal compound was TAC 141 titanium trichloride supplied by Toho Titanium Company of Japan and the phosphorus compound was Compound V that is:

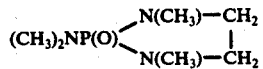

The mill was loaded under nitrogen first with TiCl$_3$ and then slowly with the phosphorus compound, the mill being agitated at room temperature (15°-20°C). The molar ratio TAC 141 to phosphorus compound was 9:1 and milling was effected at 120 rpm for 24 hours. A nitrogen atmosphere was maintained in the mill throughout.

Polymerisations were carried out as described in Example 70 and Examples 71 to 73.

The results obtained are set out in Table 10.

TABLE 10

| Example No. | Fourth Component Ref | Amount (mmol/l) | Conversion to solid polymer (g/mmol Ti) (d) | Soluble Yield (%) (e) |
|---|---|---|---|---|
| 80 | NIL | — | 43.5 | 14.1 |
| 81 | V | 3 | 42.5 | 7.5 |

(d) (e) see Table 4

EXAMPLES 82 to 84

The effect of ball-milling the transition metal compound with a further phosphorus compound of the type defined was studied.

The ball-mill used was as described for Examples 70 to 73. The transition metal compound was TAC 141 titanium trichloride supplied by Toho Titanium Company of Japan and the phosphorus compound was Compound XIII that is,

The two materials were introduced into the mill as a slurry in pentane, which was evaporated under vacuum at about 50° C before commencing the milling which was effected at room temperature (15°-20° C). The molar ratio TAC 141 to phosphorus compound was 18:1 and milling was effected at 120 rpm for 24 hours. A nitrogen atmosphere was maintained in the mill throughout.

Polymerisations were carried out as described in Example 70 and Examples 71 to 73. In a further polymerisation a quantity of an electron donor compound was added shortly after the aluminium triethyl and half an hour before adding the milled titanium trichloride.

The results obtained are set out in Table 11.

TABLE 11

| Example No. | Fourth Component Ref (f) | Amount (mmol/l) | Conversion to solid polymer (g/mmol Ti) (d) | Soluble Yield (%) (e) |
|---|---|---|---|---|
| 82 | NIL | — | 61 | 14.6 |
| 83 | XIII | 1 | 47.5 | 5.0 |
| 84 | S | 4 | 51.5 | 7.5 |

(f) Compound S is tris(dimethylamino) silicon monochloride ([(CH$_3$)$_2$N]$_3$SiCl)

EXAMPLES 85 to 87

The procedure of EXAMPLES 82 to 84 was repeated except that in the ball-milling step a molar ratio of 9:1 (TAC 141 to Compound XIII) was used and the mill was loaded under nitrogen first with TiCl$_3$ and then slowly with phosphorus compound the mill being agitated.

Polymerisations were carried out as described in Examples 82 to 84. The results obtained are set out in Table 12.

TABLE 12

| Example No. | Fourth Component Ref (f) | Amount (mmol/l) | Conversion to solid polymer (g/mmol Ti) (d) | soluble Yield (%) (e) |
|---|---|---|---|---|
| 85 | NIL | — | 45.5 | 9.1 |
| 86 | XIII | 1 | 36 | 6.3 |
| 87 | S | 4 | 46.2 | 7.1 |

(d) (e) see Table 4

EXAMPLES 88 and 89

The ball-milling procedure of Examples 85 to 87 was repeated except that the milling was effected at a temperature maintained in the range 60° to 65° C. The milled material was then used immediately to polymerise propylene as described in Examples 82 to 84 without adding a further quantity of phosphorus compound. A yield of 58 gms of polymer per mMole of titanium in the catalyst was obtained. The proportion of soluble polymer obtained was 4.5% based on the total yield of polymer. A further polymerisation was carried out 24 hours after hot milling when the proportion of soluble polymer increased to 7% the yield of polymer being 56 gms of polymer per mMole of titanium in the catalyst.

EXAMPLES 90 to 92

A catalyst system was used wherein a cyclic polyene was incorporated as a fourth catalyst component.

The procedure used was generally as described in respect of Examples 20 to 32 except that the titanium trichloride was Stauffer AA and the cyclic polyene (which was cycloheptatriene - CHT) was included in the catalyst system. The CHT was added to the aluminium triethyl before the phosphorus compound was added.

The results obtained are set out in Table 13.

EXAMPLES 93 to 96

The effect of phosphorus compounds was tested in propylene polymerisations using diethyl aluminium chloride and Stauffer AA grade titanium trichloride. (This material is believed to be obtained by the reduction of $TiCl_4$ with aluminium metal and thereafter ball-milling the dry powder).

The polymerisation conditions were as described for Examples 20 to 32 but using 10 mmol $Et_2AlCl$ and 5 mmol $TiCl_3$ per litre of inert diluent and a polymerisation time of 3 hours.

The results are set out in Table 14. Comparative example G was carried out in a similar manner but omitting the phosphorus compound.

TABLE 13

| Example or Comparative Example | Phosphorus Compound Reference | Phosphorus Compound Amount (mmol/l) | CHT Amount (mmol/l) | Conversion to solid Polymer g/mmol Ti (d) | Soluble Yield (%) (e) |
|---|---|---|---|---|---|
| 90 | I | 1 | 2 | 16 | 5.1 |
| 91 | V | 2 | 2 | 17 | 4.2 |
| 92 | XIII | 1 | 2 | 18 | 5.0 |
| F | NIL | NIL | 2 | 14 | 9.3 |
| C | NIL | NIL | NIL | 32.5 | 29.3 |

TABLE 14

| Example or Comparative Example | Phosphorus Compound Reference | Phosphorus Compound Amount (mmol/l) | Conversion to Solid Polymer (g/mmol Ti) (d) | Soluble Yield (%) (e) |
|---|---|---|---|---|
| 93 | V | 2 | 10.9 | 2.6 |
| 94 | I | 1 | 8.5 | 3.9 |
| 95 | XIII | 1 | 10.6 | 4.0 |
| 96 | III | 2 | 8.9 | 1.7 |
| G | None | — | 6.0 | 3.1 |

(d) (e) see Table 4

EXAMPLES 97 and 98

Propylene polymerisations were carried out with a catalyst the titanium trichloride component of which was obtained by reduction of $TiCl_4$ with ethyl aluminium sesquichloride by slowly adding 0.9 moles of the aluminium compound to 1.0 mole of $TiCl_4$, both compounds being dissolved in an inert hydrocarbon diluent and the reaction mixture being stirred initially at 0° C. After 6 hours the temperature of the catalyst reaction mixture was raised to 110° C and, after 4 hours, the slurry was cooled and washed with the inert hydrocarbon before the catalyst was used. The polymerisations were carried out under the conditions of Examples 93 to 96 and the results obtained are presented in Table 15 together with the results of a comparative example carried out in the absence of a phosphorus compound.

EXAMPLE 99

A 7-litre stainless steel pressure autoclave fitted with a water-circulation jacket and stirrer was vacuum purged with dry propylene and finally brought to atmospheric pressure with propylene gas at about 25° C. 36 millimoles of diethyl aluminium chloride were introduced as a 0.75 molar solution and 3 millimoles of 0.5 molar catalyst slurry. The catalyst consisted of titanium aluminium chloride maufactured by Stauffer Chemical Company as

TABLE 15

| Example or Comparative Example | Phosphorus Compound Reference | Phosphorus Compound Amount (mmol/l) | Conversion to Solid Polymer (g/mmol Ti) (d) | Soluble Yield (%) (e) |
|---|---|---|---|---|
| 97 | V | 2 | 10.4 | 1.6 |
| 98 | III | 2 | 7.3 | 0.36 |
| H | None | — | 8.3 | 1.0 |

(d) (d) See Table 4

AA grade titanium trichloride which had been milled at 120 rpm together with 0.11 moles of octamethylpyrophosphoric amide (compound XIII) per mole of $TiCl_3$ under nitrogen for 64 hours in the stainless steel mill used in Examples 70 to 73.

Directly after the addition of catalyst, 5 litres of liquid propylene were added and the autoclave heated to 65° C. Hydrogen gas was added to the autoclave in amount equal to 0.15 mole percent of the propylene. After 2½ hours the autoclave was vented and 1470 grams of polymer recovered as a free flowing powder. Analysis revealed a residue of 97 parts per million titanium in the polymer. 5.4% of the polymer was extracted by boiling heptane. The melt flow index of the polymer using a 10 kg weight at 190° C was found to be 7.2.

A comparison experiment with a catalyst which had been ball-milled omitting the octamethyl pyrophosphoramic amide gave a little lower yield of 1311 grams (analysis 109 ppm Ti). The heptane soluble polymer amounted to 8.1% i.e. the polymer was less stereoregular than that obtained using the phosphorus compound.

The proportion of heptane soluble polymer was determined by extraction with boiling heptane in a Soxhlet extractor.

EXAMPLE 100

The autoclave and procedure of Example 98 was used with 8 millimoles of triethyl aluminium in place of the diethyl aluminium chloride and ½ millimole of the same catalyst as in Example 99. No hydrogen was added. After 2½ hours, 1600 grams of polymer were obtained containing 15 ppm titanium residue. The proportion of heptane soluble polymer was 17.4%.

EXAMPLE 101

The experiment of Example 100 was repeated adding 2 millimoles of octamethyl pyrophosphoric amide to the triethyl aluminium (8 millimoles) and 1 millimole of the catalyst of Example 99. After one hour 1110 grams of polymer were obtained which analysed to a residue of 43 ppm titanium. The proportion of heptane soluble polymer was 11.5%.

A comparative example was carried out using 1.9 millimoles TAC 131 and 4.4 millimoles aluminium triethyl, in the same autoclave and adding 6 litres of liquid propylene. polymerisation was carried out overnight (about 17 hours) and the product obtained contained 99 ppm of titanium and was a sticky material containing about 60% of heptane soluble polymer.

EXAMPLE 102

An 8-litre reaction autoclave with a vertically mounted stirrer fitted so that the sides of the vessel were scraped was loaded with 400 grams of dry polypropylene carrier polymer and vacuum purged with pure dry propylene gas at 70° C. The stirrer was stopped and 6 mmol of triethyl aluminium as a 1.5 molar solution in heptane were charged. The contents of the autoclave were stirred for 5 minutes, the stirring stopped again, and 1 mmol of catalyst (Stauffer AA grade titanium trichloride which had been ball-milled with 0.11 mole of octamethyl pyrophosphoric amide as in Example 99) was added as a slurry in heptane. The stirrer was restarted and the autoclave pressurised with propylene to 400 psi gauge over 45 minutes. The polymerisation was allowed to proceed keeping the gas pressure at 400 psig for a further 1¾ hours starting at a temperature of 67° C and rising to 80° C. The autoclave was vented and polymer removed as a material which was easily broken down to a free-flowing powder. The increase in weight was 1720 grams. The polymer formed in the gas phase polymerisation contained 14.1% of polymer extractable by boiling heptane and analysed to a residual titanium content of 28 ppm.

In a repeat experiment omitting the phosphorus compound a similar yield of polymer was obtained but this was of a sticky nature and the heptane soluble polymer was about 50%.

EXAMPLES 103 and 104

The catalyst described in Example 99 was used to polymerise propylene both in the presence and absence of a further amount of a phosphorus compound using polymerisation conditions similar to those used in Examples 70 to 73. The conditions used and the results obtained are set out in Table 16.

EXAMPLE 105

Preparation of

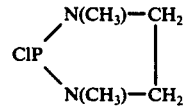

68.8 g (0.5 mole) PCl₁ and 150 mls pyridine were charged under a stream of dry nitrogen into a 500 ml three-necked flask fitted with a stirrer, condenser and dropping funnel. The flask was cooled in an ice bath and a solution of 44 g (0.5 mole) N,N'-dimethylethylene diamine in 50 mls pyridine was added dropwise under a blanket of dry nitrogen. On complete addition of the diamine the reaction mixture was stirred for 1 hour at room temperature. The solid pyridine hydrochloride was filtered off under nitrogen and washed with a small quantity of pyridine.

TABLE 16

| Example | Additional Phosphorus Compound Reference | Additional Phosphorus Compound Amount (mmol/l) | AlEt₃ (mmol/l) | Conversion to Solid Polymer (g/mmol Ti) (d) | Soluble Yield (%) (e) |
| --- | --- | --- | --- | --- | --- |
| 103 | V | 2.5 | 9.3 | 43.6 | 3.9 |
| 104 | Nil | Nil | 8.0 | 63.7 | 7.2 |

The washings and filtrate were evaporated in a rotary evaporator under reduced pressure (60 mm) and the residue fractionally distilled under reduced pressure. The fraction distilling at 70° (0.8 mm) was collected and was identified as

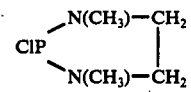

EXAMPLE 106

The phosphorus compound obtained in Example 105 was used to polymerise propylene using the technique described in Examples 20 to 32. The catalyst used consisted of 2 mmol TiCl₃ (Stauffer AA grade), 4 mmol aluminium triethyl and 2 mole of the phosphorus compound of Example 105. A yield of 14.15 gm of polymer/mmol of Ti was obtained, the proportion of soluble polymer being 10.7%.

We claim:
1. An olefine polymerisation catalyst comprising
   1. a solid halide or oxyhalide compound of a transition metal of Group IVA to VIA of the Periodic Table, wherein the said metal has a valency below its maximum;
   2. an organo-metallic compound of aluminium, or of a non-transition metal of Group II of the Periodic System, or a complex of an organo-metallic compound of a non-transition metal of Group I or II of the Periodic System, and an organo-aluminium compound; and
   3. at least one phosphorus compound selected from materials of the formula

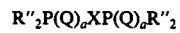

wherein
R″ is halogen, a hydrocarbyl group, a group —NR‴₂ or —OR‴, a heterocyclic group, a group (E—Z—G), or both groups R″ attached to the same P atom together form a group

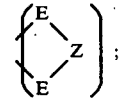

R‴ is a hydrocarbyl group; X is —O—, NR″″—, —E(CH₂)ₘE— or

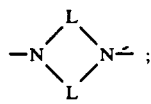

R'''' is a hydrogen atom or a hydrocarbyl group;
each L is a bivalent hydrocarbyl radical and may be the same or different;
each E is —O—, —S— or —NR'''— and may be the same or different;
G is -OR''', -SR''', -NR'''$_2$, -PR'''$_2$ or a heterocyclic ring system whereof the heteroatom is O, S, N or P;
Q is an oxygen or sulphur atom;
Z is a bivalent hydrocarbyl radical such that E and G, or E and E are separated by not more than 3 carbon atoms;
each $a$ is independently zero or one; and
$m$ is a positive integer.

2. The catalyst of claim 1 wherein the transition metal compound is titanium trichloride.

3. The catalyst of claim 1 wherein component (2) is an organo-aluminium compound which is aluminium trihydrocarbyl; or an aluminium dihydrocarbyl halide or hydride.

4. The catalyst of claim 1 which comprises 1) titanium trichloride, 2) aluminium triethyl or aluminium diethyl chloride and 3) a phosphorus compound of the formula

where R'', Q, X and $a$ are all as defined.

5. The catalyst of claim 1 wherein in the phosphorus compound the group R'' is a dialkyl amino group.

6. The catalyst of claim 1 wherein the phosphorus compound includes the group (E—Z—G) which group is derived from an alkyl glycol, an alkanolamine, a diamine or an aminothiol.

7. The catalyst of claim 1 wherein the phosphorus compound is at least one compound selected from the group consisting of

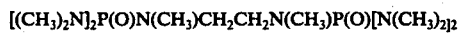
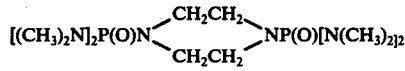
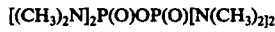
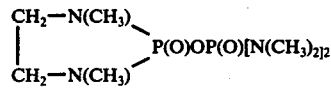
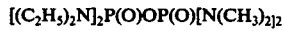

8. The catalyst of claim 1 wherein the solid halide or oxyhalide compound of the transition metal has been ground in the dry state.

9. The catalyst of claim 8 wherein the solid halide or oxyhalide compound of the transition metal has been ground with at last one compound which is a phosphorus compound of the type

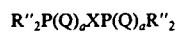

where R'', Q, X and $a$ are all as defined, or an electron donor compound which is effective to affect the catalyst activity and/or stereospecificity and is an amine, including heterocyclic amines, a diamine, an alkanolamine, an amide, urea or a derivative of urea, an organo-phosphorus compound, an organo-silicon compound, an ether, an ester, a ketone, an alcohol, or a sulphur containing analogue of ethers, esters, ketones and alcohols.

10. The catalyst of claim 9 wherein in addition to the phosphorus compound or electron donor compound which has been ground with the solid halide or oxyhalide compound of the transition metal, the catalyst, include a further quantity of at least one compound selected from said phosphorus compounds and said electron donor compounds.

11. The catalyst of claim 8 wherein the solid halide or oxyhalide compound of the transition metal has been ground with at least one compound which is a phosphorus compound of the formula

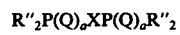

where R'', Q, X and $a$ are all as hereinbefore defined, or a phosphorus compound selected from materials of the formula

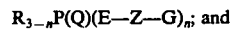

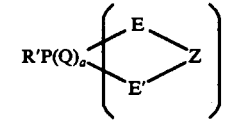

or an electron donor compound of the type which is effective to alter the activity and/or stereospecificity of the catalyst and which is an amine, including heterocyclic amines, a diamine, an alkanolamine, an amide, urea or a derivative of urea, an organo-phosphorus compound, anorgano-silicon compound, an ether, an ester, a ketone, an alcohol or a sulphur containing analogue of ethers, esters, ketones and alcohols; and the catalyst also includes a further quantity of the phosphorus compound of the formula

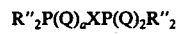

which further quantity has not been ground with the transition metal compound; wherein
each R group is independently halogen, a hydrocarbyl group, a group —NR'''$_2$, a group —OR''', or a heterocyclic group;
R' is R or the group (E—Z—G);
E' is —S' or —NR''''—; and
$n$ is 1, 2 or 3.

12. The catalyst of claim 11 wherein the further quantity of the phosphorus compound of the formula $R''_2P(Q)_aXP(Q)_aR''_2$ is not allowed to contact the solid halide or oxyhalide compound of the transition metal in the absence of the organo-metallic compound which is component (2) of the catalyst.

13. The catalyst of claim 9 wherein the solid halide or oxyhalide compound of the transition metal has been ground with at least one of said phosphorus compounds, or one of said electron donor compounds, in the molar ratio of solid halide or oxyhalide compound of the transition metal to said phosphorus compound or said electron donor compound of at least 6:1.

14. The catalyst of claim 11 wherein titanium trichloride has been modified by ball-milling with $[(CH_3)_2N]_2P(O)OP(O)[N(CH_3)_2]_2$; or
$[(CH_3)_2N]_2P(O)N(CH_3(CH_2CH_2N(CH_3)_2)$.

15. The catalyst of claim 14 wherein the catalyst includes a further component which is $[(CH_3)_2N]P(O)OP(O)[N(CH_3)_2]_2$.

16. A process for the production of an olefine polymer or copolymer wherein at least one olefine monomer is contacted with the polymerisation catalyst of claim 1.

17. The process of claim 16 wherein the catalyst there is present, for each molecular porportion of component 1), from 0.05 to 20 molecular proportions of component 2) and from 0.01 to 10 molecular proportion of component 3), the amount of component 3) not being greater than the amount of component 2).

18. The process of claim 17 wherein for each molecular proportion of component 1), there is present from 1 up to 20 molecular proportions of component 2) and from 0.1 up to 4.0 molecular proportions of component 3).

19. The process of claim 16 wherein the catalyst comprises titanium trichloride in a concentration of $C_T$ millimoles/liter; aluminium triethyl in a concentration of $C_A$ millimoles/liter and a phosphorus compound of the type $R''_2PXPR''_2$ in a concentration in the range $$\frac{C_T}{4f} \text{ to } \frac{C_A}{2f} \text{ millimoles/liter,}$$

or a phosphorus compound of the type $R''_2P(Q)XP(Q)R''_2$ in a concentration in the range $$\frac{C_T}{20} \text{ to } \frac{3C_A}{8} \text{ millimoles/liter}$$

where $f$ is the number of 0 and/or N atoms in the trivalent phosphorus compound.

20. The process of claim 16 wherein before being contacted with the polymerisation catalyst, the monomer, and any diluent used, have been subjected to an additional purification treatment.

* * * * *

UNITED STATES PATENT OFFICE  Page 1 of 2
CERTIFICATE OF CORRECTION

Patent No. 4,051,307          Dated  September 27, 1977

Inventor(s) Anthony David Caunt; Michael Stanley Fortuin

It is certified that error appears in the above-identified patent and that said Letters Patent are hereby corrected as shown below:

IN THE HEADING:

At section [30] relating to Foreign Application Priority Data, please correct the filing date of British Application No. 7985/73 to read:

--Feb. 19, 1973--.

IN THE SPECIFICATION:

At column 2, line 40, please correct "-NH'''-" to read:

-- -NR''' - --.

Column 3, line 49, "preer" should read --prefer--.

Column 4, line 58, delete in its entirety, as it is a repetition.

Column 5, at formulas XI, XII, XIII, XIV, XVII and XVIII, the final bracket is too small and is too low. In all cases it should be corrected to read:

-- . . . $[N(CH_3)_2]_2$ --.

UNITED STATES PATENT OFFICE
CERTIFICATE OF CORRECTION

Patent No. 4,051,307   Dated September 27, 1977

Inventor(s) Anthony David Caunt; Michael Stanley Fortuin

It is certified that error appears in the above-identified patent and that said Letters Patent are hereby corrected as shown below:

Column 6, line 11, "R∆" should read --R"-- (both occurrences).

IN THE CLAIMS

Claim 7, column 35, lines 45, 47, 50, 53, 61 and 62, at the end of each line, the final bracket is too low and too small. In all cases it should be corrected to read:

--. . . $[N(CH_3)_2]_2$ --.

Signed and Sealed this

Tenth Day of July 1979

[SEAL]

Attest:

Attesting Officer

LUTRELLE F. PARKER
Acting Commissioner of Patents and Trademarks